United States Patent [19]

Jorgensen

[11] Patent Number: 4,650,328

[45] Date of Patent: Mar. 17, 1987

[54] APPARATUS FOR DETERMINING THE FILLING PRESSURE OF A PLURALITY OF MICROBALLOONS

[75] Inventor: Betty S. Jorgensen, Jemez Springs, N. Mex.

[73] Assignee: The United States of America as represented by the United States Department of Energy, Washington, D.C.

[21] Appl. No.: 617,657

[22] Filed: Jun. 5, 1984

[51] Int. Cl.⁴ ............... G01N 21/01; G02B 21/34
[52] U.S. Cl. .................................. 356/244; 350/534; 376/151; 376/916
[58] Field of Search .............. 356/244; 350/534, 535, 350/536; 376/151, 152, 916

[56] References Cited

U.S. PATENT DOCUMENTS 3,899,610  8/1975  Henry ........................... 350/536 X
4,544,520 10/1985  Farnum et al. ................ 376/916 X

OTHER PUBLICATIONS

Stone et al., "Light Interference in Hollow Glass Microsphere Laser Targets" Lawrence Livermore Laboratory Report UCRL-77487, 1975.

*Primary Examiner*—Edward P. Westin
*Assistant Examiner*—Matthew W. Koren
*Attorney, Agent, or Firm*—Samuel M. Freund; Ray G. Wilson; Judson R. Hightower

[57] ABSTRACT

A simple apparatus for removably holding a plurality of microballoons during filling and determination of the pressure of the gas fill. The subject apparatus permits the manipulation of substantial numbers of microballoons necessary for the rapidly growing requirements for these capsules.

4 Claims, 2 Drawing Figures

APPARATUS FOR DETERMINING THE FILLING PRESSURE OF A PLURALITY OF MICROBALLOONS

This invention is the result of a contract with the Department of Energy (Contract No. W-7405-ENG-36).

BACKGROUND OF THE INVENTION

The present invention relates generally to the manipulation of microballoons, and more particularly to an apparatus for removably holding a plurality of microballoons in order to more efficiently carry out the filling of the microballoons with a known quantity of gas.

Glass microballoons filled with various gases are used for laser fusion targets in order to facilitate diagnosis of laser-target interaction by x-ray or radiochemical techniques and for shock-wave diagnostics. Such microballoons are currently filled with gases of interest by first perforating the microballoon with focused, high-intensity laser radiation, applying an uncured epoxy over the hole, and loading the microballoons into a pressure vessel which is first evacuate and then filled with the gas or gas mixture of interest, and finally heated for several hours to cure the epoxy. That is, the gas invades the microballoon while the epoxy is curing and cannot readily escape once the epoxy cures. Since it has been observed that permeation of the gas occurs through the glass walls of the microballoons or through the cured epoxy occurs, it is important to nondestructively measure the gas pressure inside the microballoons as close to their time of use as is possible. One successful technique for accomplishing this purpose involves the use of interferometry.

In "Measurement of Laser Fusion Capsules Using the Interferometer Method of Excess Fractions" by Roger R. Stone et al., Lawrence Livermore Laboratory Report UCRL-77487 (1975), the author describes an interferometric method of nondestructively determining the gas pressure inside of gas-filled microballoons using an interferometric technique. It is critical to the measurement that the interferometer "view" the microballoon from the identical perspective in both the unfilled and the filled configurations in order that the gas located inside of the microballoon give rise to a change in the interferometric pattern of the gas plus microballoon which can be related to the pressure of that gas therein. Additionally, the process of producing individual gas-filled microballoons is described in "Laser Fusion Targets Containing Gas Not Permeable Through A Wall: A Technique For Fabrication," by S. Butler and B. Cranfill Jorgensen, LA-UR-79-2468 (1979). However, requirements for thousands of microballoons has necessitated the development of more efficient procedures for handling and processing microballoons.

SUMMARY OF THE INVENTION

Accordingly, it is the principal object of this invention to provide an apparatus for the handling of a plurality of microballoons during gas filling and pressure measurement procedures.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combination particularly pointed out in the appended claims.

To achieve the foregoing and other objects, and in accordance with the purposes of the present invention, as embodied and broadly described herein, the apparatus hereof includes an optically transparent, essentially flat plate having a rod affixed in a substantially parallel manner to a flat surface of the plate. The rod has a sticky substance applied thereto which is selected such that the microballoons can be sufficiently rigidly affixed to the rod that the process of filling the microballoons with gas and measuring the gas pressure can be efficiently achieved and the microballoons removed for use without damage to them. The filling process includes the steps of scanning the microballoons individually in order to generate an interferometric pattern characteristic of each microballoon under investigation, perforating the microballoon with high intensity laser radiation, filling the microballoon with a gas not permeable through the walls of the microballoons, sealing the microballoons and individually rescanning them in order to obtain a second interferometric pattern of the microballoons filled with gas which can be related to the gas pressure therein. The interferometry is performed through the flat plate in order to avoid the sticky substance which affixes the microballoons to the rod. Preferably, the sticky substance includes silastic adhesives such as RTV. It is also preferred that the optically transparent plate include a glass microscope slide. Preferably also, the rod is a glass rod.

The apparatus of the instant invention then permits the efficient processing of large numbers of microballoons to prepare these microballoons for use as targets for inertial confinement experiments as well as for shock-wave detection.

BRIEF DESCRIPTION OF THE DRAWINGS

The accompanying drawings, which are incorporated in and form a part of the specification, illustrate one embodiment of the present invention and, together with description, serve to explain the principles of the invention.

FIG. 2 shows a schematic representation of the microballoon holder of the subject invention described in FIG. 1 hereof in cooperation with a transmission interferometric microscope.

DETAILED DESCRIPTION OF THE INVENTION

Figure 1:
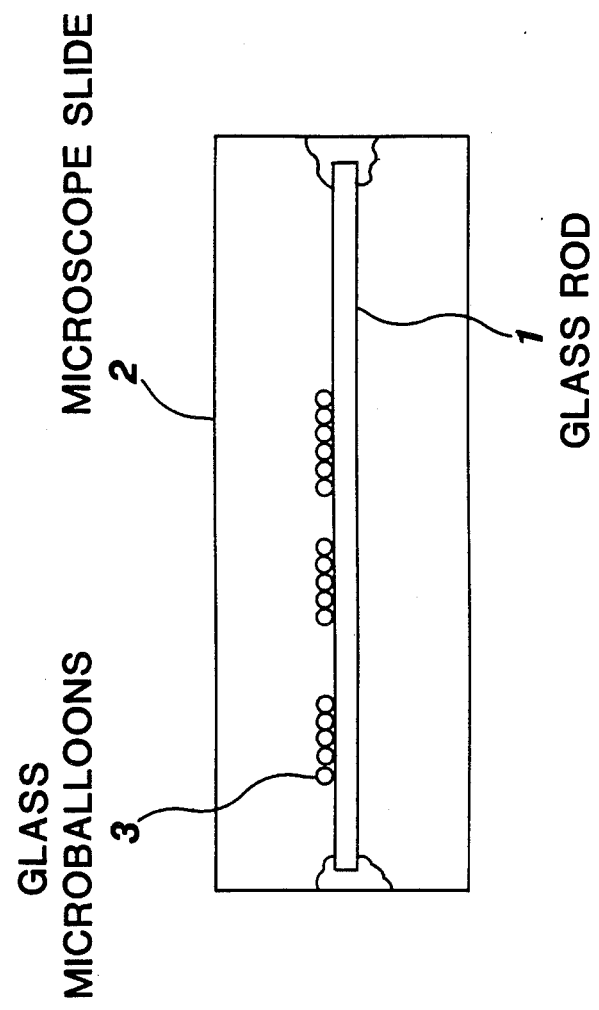
FIG. 1 shows a schematic representation of the microballoon holder of the subject invention showing the relationship among the flat plate, the rod and the microballoons to be removably held in place.

Reference will now be made in detail to the present preferred embodiment of the invention, an example of which is illustrated in the accompanying drawings. Turning now to FIG. 1, the relationship among the flat plate, the rod and the microballoons is shown schematically therein. In the preferred embodiment of the subject invention, the flat plate actually utilized was a glass microscope slide 2. A glass rod 1 was affixed onto one of the two larger flat surfaces of the slide in a substantially parallel relationship to this surface. The glass microballoons were removably affixed to the rod by means of a silastic adhesive such as 3140 RTV which is a trade name of Dow Corning. The laser perforation process and the subsequent application of epoxy to the hole produced thereby were then performed, and the interferometric determinations made before, to establish a base pattern, and after the manipulation of the microballoons attendant to their filling. It is essential that the position of the microballoons is not disturbed during the perforation, filling and epoxying since the interferometric pressure determination relies on the difference in the interferometer patterns for the empty and filled microballoons, and measuring a microballoon in a region where the wall thickness might be different in the second measurement would create an error in the pressure determination. The individual microballoons are placed on the apparatus of the instant invention by first moving them using a fine glass probe on the end of which is placed a small quantity of adhesive with which a microballoon is held in place. The microballoon is then transferred to its desired position on the glass rod previously coated with a similar adhesive. The adhesive used to remove the microballoon from the glass probe then holds the microballoon in place during the above-described operations, yet is insufficiently strongly bound to the microballoons to prevent their removal by the use of another adhesive-tipped probe.

FIG. 2 shows the microballoon holder described in FIG. 1 hereof in cooperation with a transmission interferometer microscope 4 which utilizes the Jamin-Lebedeff technique for obtaining interferograms. The apparatus is calibrated to obtain a filling curve for the particular gas used. Clearly, other interferometric microscope arrangements would be apparent to an individual having ordinary skill in the interferometer art area after reading the disclosure for the subject invention.

The instant invention therefore permits the sequential processing of a plurality of microballoons by the insertion of the glass slide into a reproducible positioning device which can locate an individual microballoon with precision for perforation using a laser beam and also in the interferometer utilized for the pressure determinations. Each microballoon can be measured in turn.

The foregoing description of the preferred embodiment of the invention has been presented for purposes of illustration and description. It is not intended to be exhaustive or to limit the invention to the precise form disclosed, and obviously many modifications and variations are possible in light of the above teaching.

The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What I claim is:

1. An apparatus for determining the filling pressure of a plurality of microballoons, which comprises in combination:
    a. an optically transparent plate having a substantially flat surface;
    b. a rod affixed to the substantially flat surface of said optically transparent plate for removably attaching the microballoons, said rod being located substantially parallel to said transparent plate, and having a sticky substance thereon; and
    c. means for interferometrically scanning each of the microballoons both before and after the filling thereof in order to determine the gas fill pressure, the individual microballoons being attached sufficiently rigidly to said rod to permit said means for interferometrically scanning each of the microballoons to measure substantially the same microballoon orientation before and after the filling thereof.

2. The apparatus as described in claim 1, wherein said sticky substance includes silastic adhesive.

3. The apparatus as described in claim 2, wherein said optically transparent plate includes a glass microscope slide.

4. The apparatus as described in claim 3, wherein said rod includes glass rod.

* * * * *